United States Patent [19]
Cohen et al.

[11] Patent Number: 5,878,373
[45] Date of Patent: Mar. 2, 1999

[54] SYSTEM AND METHOD FOR DETERMINING THREE-DIMENSIONAL STRUCTURE OF PROTEIN SEQUENCES

[75] Inventors: Fred E. Cohen, San Francisco; Thomas R. Defay, San Bruno, both of Calif.

[73] Assignee: Regents of the University of California, San Francisco, Calif.

[21] Appl. No.: 761,724

[22] Filed: Dec. 6, 1996

[51] Int. Cl.$^6$ .............................. G06F 19/00; G06F 17/00
[52] U.S. Cl. ................................. 702/22; 702/19
[58] Field of Search .................................. 364/496, 497, 364/498, 499, 578; 702/22, 19

[56] References Cited

U.S. PATENT DOCUMENTS

| | | | |
|---|---|---|---|
| 5,436,850 | 7/1995 | Eisenberg et al. | 364/496 |
| 5,701,256 | 12/1997 | Marr et al. | 364/496 |

OTHER PUBLICATIONS

Chan, S.C. et al A Survey of Multiple Sequence Comparison Methods Bulletin of Mathematical Biology, vol. 54, No. 4, pp. 563–598, 1992.

*Primary Examiner*—Lila Feisee
*Assistant Examiner*—Nirmal S. Basi
*Attorney, Agent, or Firm*—Gary S. Williams; Flehr Hohbach Test Albritton & Herbert LLP

[57] ABSTRACT

The present invention pertains to a system and method for predicting the protein fold of a target amino acid residue sequence of unknown protein structure. A target sequence is represented by a sequence of residue variability types that utilizes positional variability information present in an associated family of homologous sequences to the target sequence. The use of the positional variability information increases the likelihood of matching the target sequence with a known protein structure. In a first preferred embodiment, a target sequence is mapped into a sequence of residue variability types that are based on the solubility variability present between amino acid residues in homologous sequences. In a second preferred embodiment, each residue variability type represents a cluster of residue types at each position of aligned sets of homologous protein sequences. Each distinct cluster represents a pattern of residue variability at various positions in sets of homologous protein sequences. The sequence of residue variability types is aligned with one or more environment strings, each of which represents a known protein structure in accordance with the degree of surface exposure for each amino acid position in the protein's structure. The alignment is performed using a threading procedure that determines a score for each alignment indicating the compatibility of the sequence to the structure. The protein structure associated with the highest score is deemed to be the most analogous structure to the target sequence.

53 Claims, 8 Drawing Sheets

Scoring Matrix
120

|   | RVT$_1$ | RVT$_2$ | RVT$_3$ | ... | RVT$_n$ |
|---|---|---|---|---|---|
| E |   |   |   |   |   |
| P |   |   |   |   |   |
| B |   |   |   |   |   |

FIG. 2B

Dynamic Programming Matrix
124

Residue Variability Type Sequence of Unknown Protein Structure

Environment String of Known Protein Structure

FIG. 2C

SYSTEM AND METHOD FOR DETERMINING THREE-DIMENSIONAL STRUCTURE OF PROTEIN SEQUENCES

This invention was made with Government support under Grant No. GM39900, awarded by the National Institutes of Health. The government has certain rights in this invention.

The present invention relates generally to protein structure prediction and particularly to identifying a known protein structure that is compatible with a target sequence and its associated multiple sequence alignment.

BACKGROUND OF THE INVENTION

Proteins (or polypeptides) are linear polymers of amino acids. The polymerization reaction which produces a protein results in the loss of one molecule of water from each amino acid, and hence proteins are often said to be composed of amino acid residues. Natural protein molecules may contain as many as 20 different types of amino acid residues. The particular linear sequence of amino acid residues in a protein defines the primary sequence, or primary structure, of the protein. The primary structure of a protein can be determined with relative ease using known methods.

Proteins fold into a three-dimensional structure. The folding is determined by the sequence of amino acids and by the protein's environment. Examination of the three-dimensional structure of numerous natural proteins has revealed a number of recurring patterns. Patterns known as alpha helices, parallel beta sheets, and anti-parallel beta sheets are the most common observed. A description of such protein patterns is provided by Dickerson, R. E., et al. in *The Structure and Action of Proteins*, W. A. Benjamin, Inc. California (1969). The assignment of each amino acid residue to one of these patterns defines the secondary structure of the protein. The helices, sheets, and turns of a protein's secondary structure pack together to produce the folded three-dimensional, or tertiary, structure of the protein.

In the past, the three-dimensional structure of proteins has been determined in a number of ways. Perhaps the best known way of determining protein structure involves the use of the technique of x-ray crystallography. A general review of this technique can be found in *Physical Biochemistry*, Van Holde, K. E. (Prentice-Hall, New Jersey 1971), pp. 221–239, or in Physical Chemistry with Applications to the Life Sciences, D. Eisenberg & D. C. Crothers (Benjamin Cummings, Menlo Park 1979). Using this technique, it is possible to elucidate the three-dimensional structure with good precision. Additionally, protein structure may be determined through the use of the techniques of neutron diffraction, or by nuclear magnetic resonance (NMR). See, e.g., *Physical Chemistry*, 4th Ed. Moore, W. J. (Prentice-Hall, New Jersey 1972) and NMR of Proteins and Nucleic Acids, K. Wuthrich (Wiley-Interscience, New York 1986).

The three-dimensional structure of many proteins may be characterized as having internal surfaces (directed away from the aqueous environment in which the protein is normally found) and external surfaces (which are exposed to the aqueous environment). Through the study of many natural proteins, researchers have discovered that hydrophobic residues (such as tryptophan, phenylalanine, leucine, isoleucine, valine, or methionine) are most frequently found on the internal surface of protein molecules. In contrast, hydrophilic residues (such as aspartate, asparagine, glutamate, glutamine, lysine, arginine, serine, and threonine) are most frequently found on the external protein surfaces. The amino acids alanine, cysteine, glycine, histidine, proline, serine, tyrosine, and threonine are encountered with more nearly equal frequency on both the internal and external protein surfaces.

The biological properties of proteins depend directly on the proteins three-dimensional (3D) conformation. The 3D conformation determines the activity of enzymes, the capacity and specificity of binding proteins, and the structural attributes of receptor molecules. Because the three-dimensional structure of a protein molecule is so significant, it has long been recognized that a means for readily determining a protein's three-dimensional structure from its known amino acid sequence would be highly desirable. However, it has proved extremely difficult to make such a determination. One difficulty is that each protein has an astronomical number of possible conformations (about $10^{16}$ for a small protein of 100 residues; see K. A. Dill, *Biochemistry*, 24, 1501–1509, 1985), and there is no reliable method for picking the one conformation stable in aqueous solution. A second difficulty is that there are no accurate and reliable force laws for the interaction of one part of a protein with another part, and with water. Proteins exist in a dynamic equilibrium between a folded, ordered state and an unfolded, disordered state. These and other factors have contributed to the enormous complexity of determining the most probable relative 3D location of each residue in a known protein sequence.

Sequence alignment represents one approach that has generated some success at determining a protein's three-dimensional structure from an associated amino acid sequence. Typically, sequence alignment aligns a target residue sequence of unknown three-dimensional protein structure with residue sequences of known three-dimensional protein structures. If a sequence relationship can be found, it can often be inferred that the protein of known sequence but unknown structure adopts a fold similar to the protein of known structure. This strategy works well for closely related sequences, but structural similarities can go undetected as the level of sequence identity drops below about 25 percent. In this case, a similar technique referred to as a threading procedure can be used. In a threading procedure, a target sequence of unknown protein structure is aligned with a one-dimensional representation of a protein structure.

In one such threading procedure, target sequences of unknown protein structure are aligned with profiles representing the structural environments of the residues in known three-dimensional protein structures. The method starts with a known three-dimensional protein structure and determines three key features of each residue's environment within the structure: (1) the total area of the residue's side-chain that is buried by other protein atoms, inaccessible to solvent; (2) the fraction of the side-chain area that is covered by polar atoms (O, N) or water; and (3) the local secondary structure. Based on these parameters, each residue position is categorized into an environment class. In this manner, a three-dimensional protein structure is converted into a one-dimensional environment string, which represents the environment class of each residue in the folded protein structure. A 3D structure profile table is then created containing score values that represent the frequency of finding any of the 20 common amino acids structures at each position of the environment string. These frequencies are determined from a database of known protein structures and aligned sequences. The method determines the most favorable alignment of a target protein sequence to the residue positions defined by the environment string by calculating a "best fit" alignment score for the target sequence.

The above method has been successful in associating protein folds with compatible sequences in some particular cases and in other cases has performed poorly. Thus, the method is not reliable enough for widespread application. Accordingly, it would be desirable to develop a method that has a higher assurance of predicting the protein structure of a sequence having an unknown protein structure.

An object of the present invention is to provide a method and system that predicts the three-dimensional protein structure that an amino acid sequence folds into.

It is another object of the present invention to utilize structural information inherent in a family of aligned amino acid residue sequences in order to predict the protein structure of a residue sequence of unknown structure.

It is another object of the present invention to utilize residue variability information inherent within homologous protein sequences for protein structure prediction.

Another object of the present invention is to model protein structures as a simplified structural environmental-sequence for use in protein structure prediction.

It is a further object of the present invention to model known protein structures as a one-dimensional environmental string utilizing structural characteristics of the amino acid residues with respect to each residue's degree of exposure within the structure.

SUMMARY OF THE INVENTION

The present invention pertains to a system and method for predicting the protein fold of a target amino acid residue sequence of unknown protein structure. A target sequence is represented as a sequence of residue variability types that exploits positional variability information present in an associated family of homologous sequences. The use of positional variability information increases the likelihood of matching the target sequence with a known protein structure.

In a first preferred embodiment, a target sequence is mapped into a sequence of residue variability types that are based on the solubility variability present between amino acid residues in homologous sequences. Each residue variability type represents an amino acid residue categorized into one of four solubility variability classes. The solubility variability classes are based on the hydrophobic and hydrophilic variability between each residue's position in an aligned set of homologous sequences. More particularly, each of the twenty amino acid residues can be categorized into one of the following four classes: (1) hydrophobic invariant, hydrophilic invariant; (2) hydrophobic invariant, hydrophilic variant; (3) hydrophobic variant, hydrophilic invariant; and (4) hydrophobic variant, hydrophilic variant.

In a second preferred embodiment, the solubility variability classes are based on the hydrophilic variability between each residue's position in the multiple sequence alignment. Thus, each of the twenty amino acid residues can be categorized into one of the following three classes: (1) hydrophilic variant, (2) hydrophilic invariant; and (3) hydrophilic partially variant.

In a third preferred embodiment, each residue variability type represents a cluster of residue types at each position of aligned sets of homologous protein sequences. The cluster characterization is based on the realization that a recurring pattern of variation exists in single positions and in short segments of contiguous positions in aligned sets of homologous sequences. A cluster is represented as a cluster vector that is associated with a residue location in a sequence space. Each distinct cluster vector represents a pattern of residue variability at various positions in sets of homologous protein sequences.

Each position in a set of multiple sequence alignments is mapped into a residue vector that represents the frequency of occurrence of each distinct amino acid at that sequence position. The residue vector is then associated with a closest cluster vector. The sequence of residue variability types then consists of a sequence of clusters.

A target sequence is mapped into a sequence of residue variability types, either based on solubility variability or residue positional variability (or clusters). The sequence is then compared with one or more environment strings, each of which represents a known protein structure. The environment string characterizes a known protein structure with respect to the degree of surface exposure of each amino acid in the protein's structure. The environment string utilizes three classifications which preferably includes exposed, buried, and partially buried.

The target sequence of residue variability types is aligned to each environment string using a threading procedure. The preferred threading procedure employs a dynamic programming procedure. As input to the dynamic programming procedure a table of scores is used. Each score represents the frequency of occurrence of each residue variability type of a target sequence in each environment class of a particular protein structure's environment string. The dynamic programming procedure calculates a best fit score indicating the outcome of the alignment. The protein structure associated with the highest best fit score indicates the most analogous protein structure of the target sequence.

In a fourth preferred embodiment, the protein structure of a target sequence is determined by using both residue variability type classification schemes. The protein structure determination procedure is executed once with the residue variability types characterized in accordance with the solubility classification scheme and a second time with the residue variability types classified in accordance with the clustering or residue positional variability scheme. Based of the results of both calculations, a user is provided with a confidence level indicating the likelihood that the target sequence is analogous to the predicted protein structure. When both schemes produce the same result, a higher level of confidence is associated with the predicted protein structure. When the results differ, a structural comparison of both predicted protein structures is made in order to determine several measures indicating structural similarity. If one of the structural similarity measures is within a prescribed threshold, the structures are deemed similar, resulting in the higher confidence level.

BRIEF DESCRIPTION OF THE DRAWINGS

Additional objects and features of the invention will be more readily apparent from the following detailed description and appended claims when taken in conjunction with the drawings, in which:

FIG. 2B illustrates the scoring matrix used in the preferred embodiments of the present invention.

FIG. 2C illustrates a matrix used during the computation of a score indicative of the alignment between a target sequence of residue variability types to an environment string of a known protein structure in the preferred embodiments of the present invention.

DESCRIPTION OF THE PREFERRED EMBODIMENT

Terminology

For the purposes of this document, the following pairs of terms are used interchangeably: "fold" and "protein structure"; and "target sequence" and "target sequence of unknown protein structure."

The terms "homologous sequences" and "family of homologous sequences" refer to sets of protein sequences that have a high degree of sequence similarity, and thus are known to have similar three dimensional structure. The protein sequences in a family of homologous sequences are often known or assumed to be evolutionarily related to each other.

The term "multiple sequence alignments" is defined to mean an aligned set of homologous sequences such as: (1) a target protein sequence and a family of homologous sequences; and (2) a primary protein sequence associated with a known protein structure and its family of homologous sequences.

Overview of the "Theory of the Invention"

The terms "residue variability" and "residue variability type" concern a central concept behind the present invention. In summary, it is a premise of the present invention that one is more likely to be able to match a target protein sequence with one of the known protein structures in a protein structure database if one uses the "residue variability" information in a family of homologous protein sequences to try to find a best match than if one uses only the information associated with the target protein sequence.

More specifically, given an aligned set of homologous sequences, one can mathematically quantify the range of protein residues found at each sequence position in the set of homologous sequences. At some sequence positions, the protein residues found will be highly consistent, while at other positions they will be more variable. There are numerous ways in which such residue variability can be defined and mathematically modeled, three of which are used in the preferred embodiments of the present invention.

In the preferred invention, each protein residue in a target protein sequence is mapped into one of N residue variability types, where each residue variability type represents a range or class of residue variability found at various protein sequence positions. In the preferred embodiments, the number of distinct residue variability types ranges from 60 to 80, but the number of residue variability types could be higher or lower in other embodiments. The target protein sequence, in which each sequence position is originally represented as one of 20 amino acid residues, is remapped by the residue variability type mapping process into a sequence of residue variability types. The residue variability type sequence representing a target protein is then compared with the known protein structures in a protein structure database, using an alignment scoring technique to find the best match.

System Architecture

Figure 1:
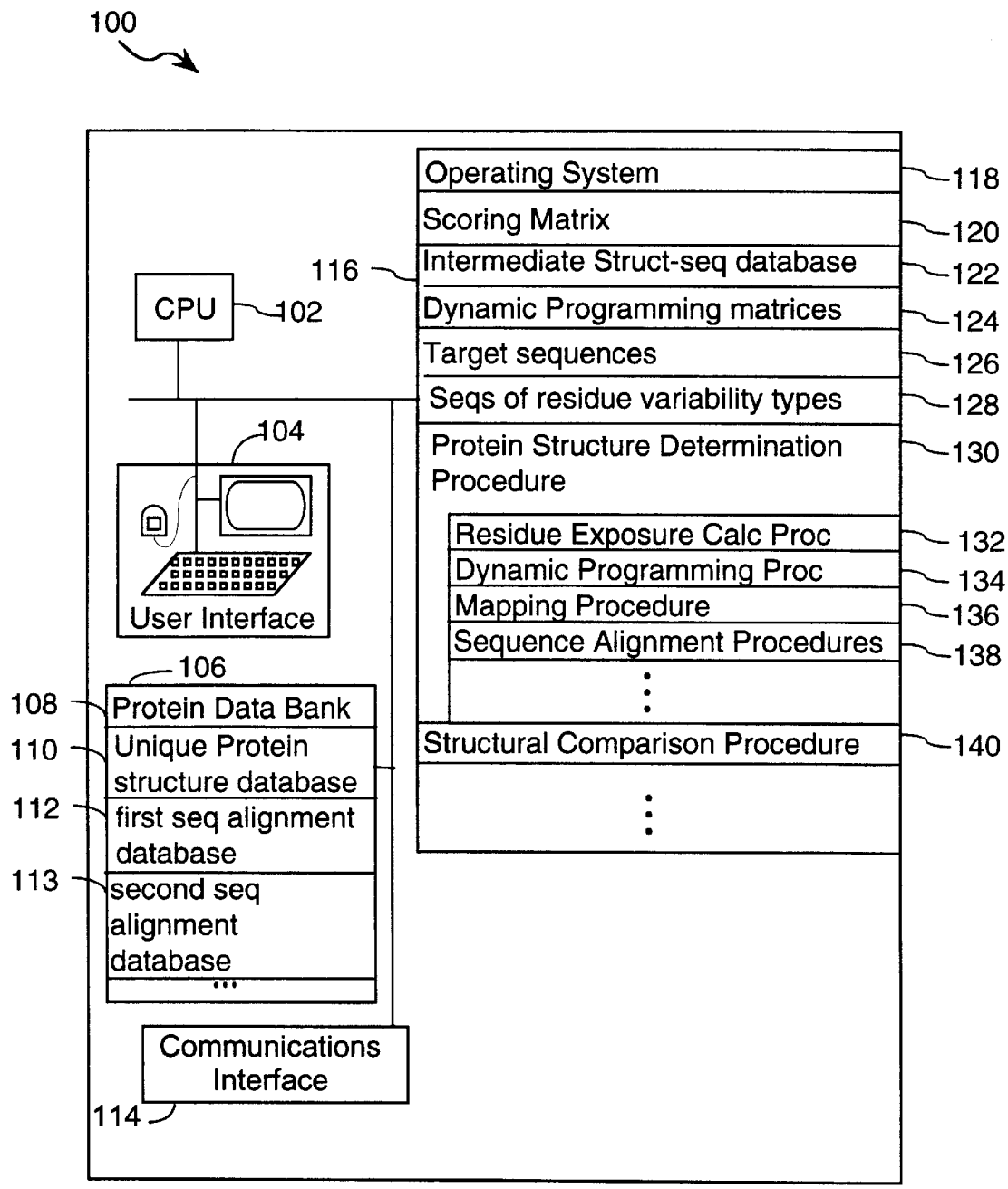
FIG. 1 is a block diagram of a computer system incorporating the preferred embodiments of the present invention.

Referring to FIG. 1, there is shown a computer system 100 for storing and providing user access to data in stored databases. The system 100 includes a central processing unit (CPU) 102, a user interface 104, a secondary memory 106, a communications interface 114, and a primary memory 116. The communications interface 114 is used to communicate with other user workstations as well as other system resources not relevant here.

The secondary memory 106 is typically magnetic disc storage that can store the following:

- a protein data bank 108 (PDB) storing a number of known protein structures and their corresponding three-dimensional coordinate information;
- a unique protein database 110 that stores a number of unique or non-redundant protein structures and their corresponding family of alignments;
- a first sequence alignment database 112 that stores primary amino acid residue sequences and their homologous residue sequences;
- a second sequence alignment database 113 that stores primary amino acid residue sequences and their homologous residue sequences for selected protein structures; and
- other databases and information.

The primary memory 116 of the computing system 100 may be implemented as RAM (random access memory) or a combination of RAM and non-volatile memory such as magnetic disk storage. The primary memory 116 of the computing system 100 can contain the following:

- an operating system 118;
- a scoring matrix 120 that associates a score with each residue variability type in a target sequence with respect to a set of environmental classes for a select set of known protein structures;
- an intermediate structure-sequence database 122 that is generated during the course of the protein structure determination procedure 130;
- a matrix 124 used by the dynamic programming procedure 134 while determining a best global alignment between a target protein sequence and another protein sequence, with one dimension of the matrix 124 representing the environmental string of a known protein structure and a second dimension of the matrix representing the residue variability type sequence of the target protein sequence;
- one or more target sequences of unknown protein structure 126;
- one or more sequences of residue variability types 128, each sequence corresponding to a particular target protein sequence of unknown protein structure 126;
- a protein structure determination procedure 130 that can contain the following:
  - a residue exposure calculation procedure 132 for determining the surface area exposure of each residue in a protein structure;

a dynamic programming procedure 134 for aligning a target sequence with one or more environment strings representing known protein structures;

a mapping procedure 136 for mapping a target protein sequence of unknown protein structure into a corresponding sequence of residue variability types;

sequence alignment procedures 138 that obtain homologous sequences for a target or primary residue sequence;

a structural comparison procedure 140; and other procedures and data structures.

Data Structures

Figure 2A:
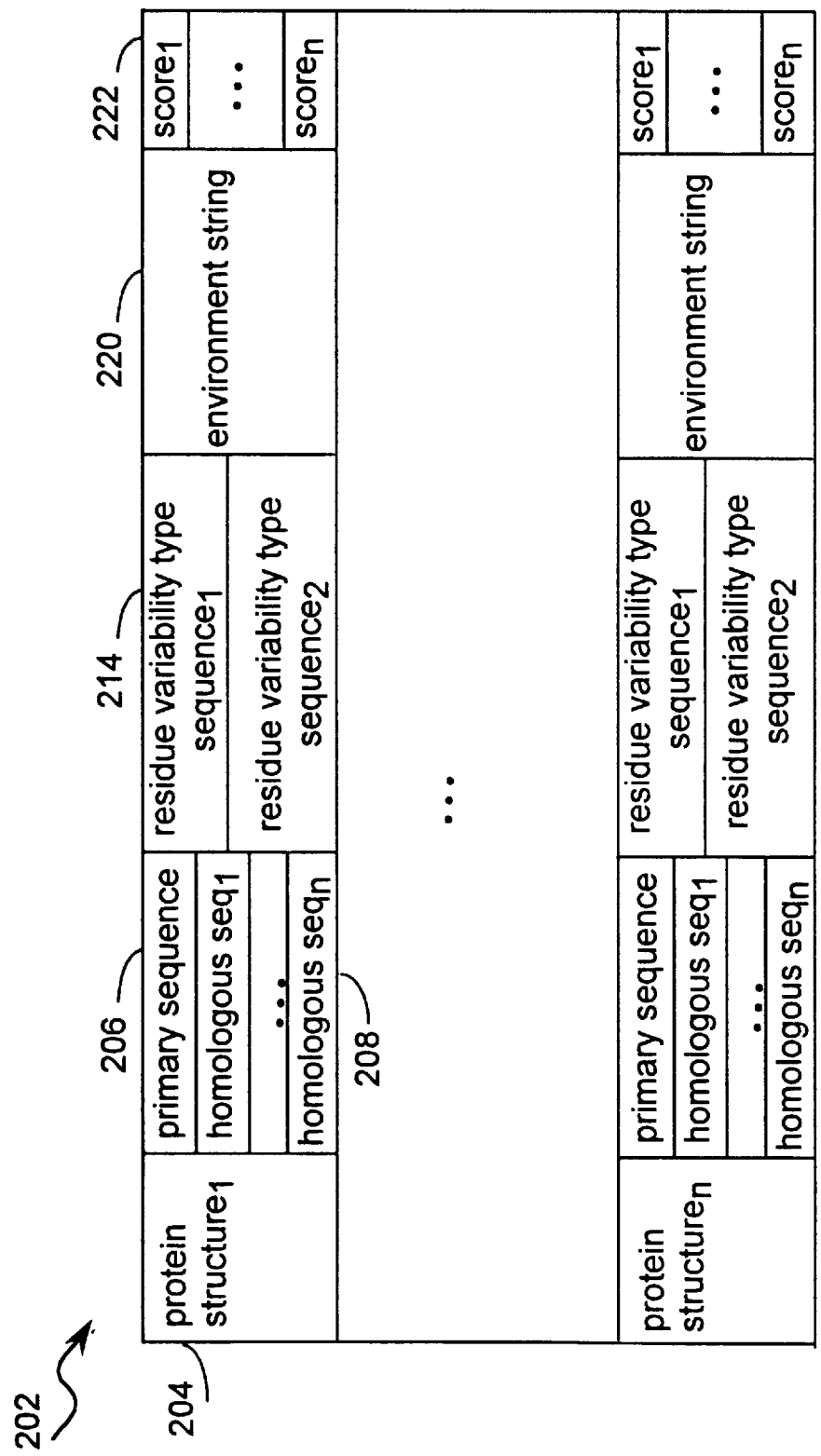
FIG. 2A illustrates the intermediate structure-sequence database that is used by the protein structure determining procedure in the preferred embodiments of the present invention.

FIGS. 2A–2C represent the main data structures used by the protein structure determination procedure 130. FIG. 2A represents the structure of the intermediate sequence-structure database 122 that can contain for each select protein structure 204: a primary residue sequence 206; one or more homologous sequences 208; one or more residue variability type sequences 214; an environment string 220; and one or more scores 222. A more detailed description of each of these components will be described below.

FIG. 2B illustrates the scoring matrix 120 that contains n columns and m rows. Each column represents one of the residue variability types ($RVT_n$) and each row represents one of the environment classes (E, P, B).

FIG. 2C illustrates a matrix 124 that consists of n columns and m rows. Each of the n columns represent one of the residue variability types present in a target sequence and each of the m rows represent one of the environment classes present in an environment string representing a known protein structure.

Although FIGS. 2A–2C represent an exemplary representation of the main data structures used by the protein determination procedure 130, the present invention is not constrained to these representations. Others may be used that provide the same functionality.

Overview of the Protein Structure Determination Procedure

Figure 3:
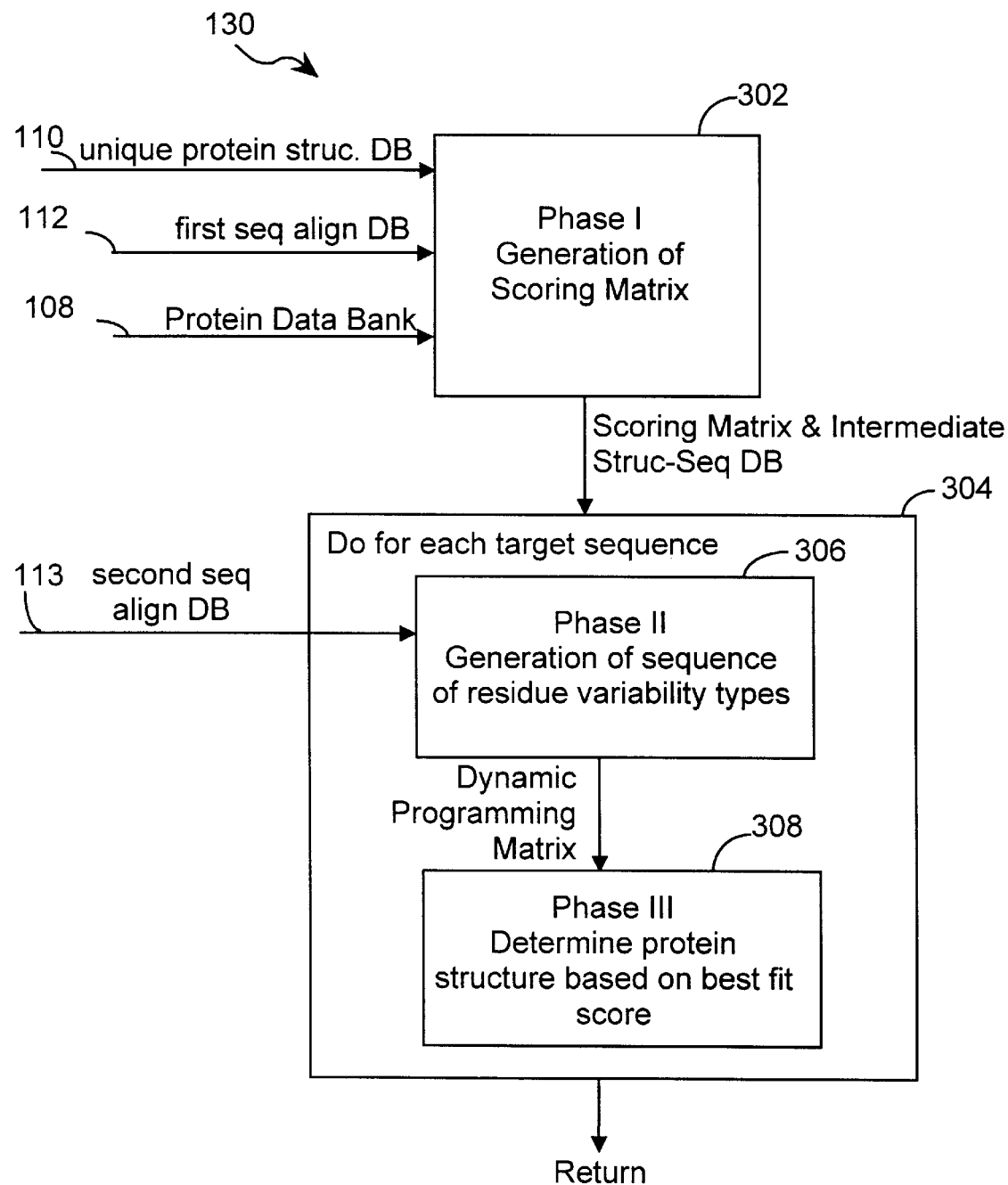
FIG. 3 is a flow chart of the steps used in the protein structure determination procedure of the present invention.

FIG. 3 illustrates the basic structure of the protein structure determination procedure 130 which can be divided into three phases. A more detailed description of each phase is detailed below. In a first phase, a scoring matrix 120 is generated (step 302). The scoring matrix represents the frequency of occurrence of each residue variability type in each environment class for a set of non-redundant known protein structures. The scoring matrix 120 utilizes a unique protein structure database 110, a first sequence alignment database 112, and a protein data bank 108. In addition, information that is used to generate the scoring matrix 120 is stored in the intermediate structure-sequence database 122 (step 302).

A second and third phase is executed for each target sequence 126 for which the protein structure determination procedure 130 is used to find an analogous protein structure (step 304). The second phase maps a particular target sequence 126 into a corresponding sequence of residue variability types 128 as will be described in more detail below (step 306).

In the third phase, the sequence of residue variability types 128 is aligned with several environment strings of known protein structures. The alignment is performed using a dynamic programming procedure in order to determine a best fit score indicative of the outcome of the alignment. The protein structure corresponding to the environment string having the highest best fit score is selected as the most probably analogous protein structure of the target sequence (step 308).

Generation of the Scoring Matrix

The first phase of the protein structure determination system and method generates a scoring matrix 120. The scoring matrix 120 is a two-dimensional table which represents in one dimension each residue variability type and in a second dimension each environment class. Preferably, there are three environment classes: exposed, buried, and partially buried. In a first preferred embodiment, there are eighty (80) residue variability types derived from expanding each of the 20 common amino acid residues into each of the following four classes: (1) hydrophobic invariant, hydrophilic variant; (2) hydrophobic invariant, hydrophilic invariant; (3) hydrophobic variant, hydrophilic invariant; and (4) hydrophobic variant, hydrophilic variant. In a second preferred embodiment, sixty (60) residue variability types can also be used which are derived from expanding each of the 20 common amino acid residues into each of the following three classes: (1) hydrophilic variant; (2) hydrophilic invariant; and (3) hydrophilic partially variant.

Each element of the scoring matrix 120 represents the likelihood of finding a particular residue variability type in a particular environment class. The scoring matrix 120 is unique in that it is based on the structural environments of residues in a known three-dimensional structure and a positional variability within a family of homologous sequences. Thus the scoring matrix 120 establishes a connection between a known three-dimensional protein structure, represented as a one-dimensional environment string, and an unknown three-dimensional protein structure, represented as a one-dimensional residue variability type sequence.

Figure 4:
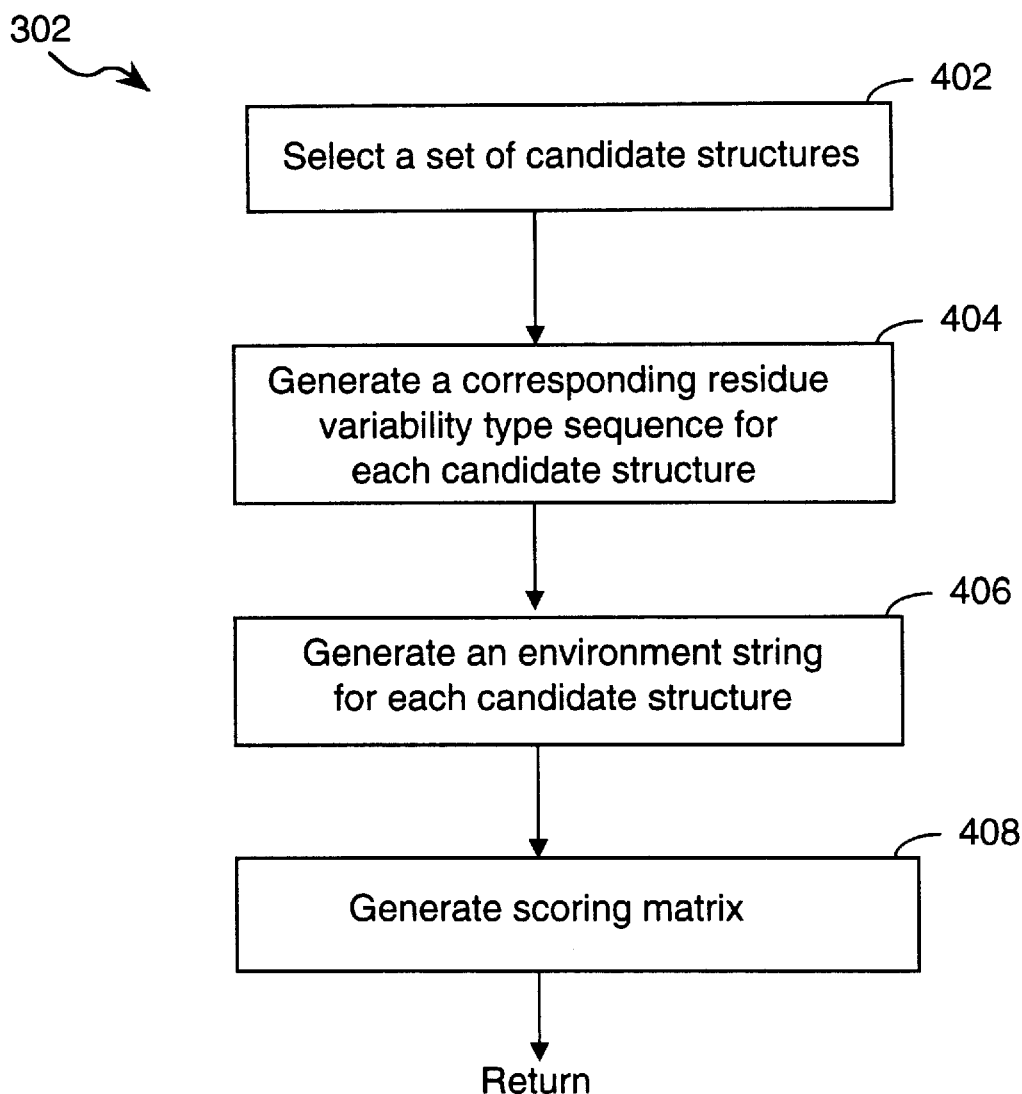
FIG. 4 is a flow chart of the steps used to generate a scoring matrix in the preferred embodiments of the present invention.

FIG. 4 illustrates the steps used in generating the scoring matrix 120. The scoring matrix 120 is generated from a select set of unique three-dimensional protein structures, their associated primary residue sequence and homologous sequences, and their three-dimensional atomic coordinates. The set of unique protein structures is selected from the database of unique protein structures 110 and a first sequence alignment database 112. Preferably, the Hobohm database of unique protein structures is used and described in Hobohm, U., Scharf, M., Schneider, R. & Sander, C., "Selection of Representative Protein Data Sets," *Protein Science* 1, 409–417 (1992) which is hereby incorporated by reference as background information.

The HSSP database of aligned sequences is used to determine the family of homologous residue sequences for the unique protein structures listed in the Hobohm database. The HSSP database is described in Sander, C. & Schneider, R., "Database of Homology-Derived Protein Structures and the Structural Meaning of Sequence Alignment," *PROTEINS: Structure, Function and Genetics* 9, 56–58 (1991), which is hereby incorporated by reference as background information.

Protein structures having a high resolution structure (<2.5 Å resolution) and having greater than 15 homologous sequences are selected from the Hobohm database (step 402). Each selected protein structure 204 is stored in the intermediate structure-sequence database 122 (see FIG. 2A) along with its primary 206 and homologous sequences 208 which are obtained from the HSSP database 112.

For each selected protein structure 204, a mapping procedure 136 is utilized to map its primary and homologous sequences into a corresponding residue variability type sequence 214 (step 404). A residue variability type is a classification scheme based on the residue positional variability present in a family of homologous sequences. The present invention encodes the residue variability inherent within a family of homologous sequences in order to characterize the range of protein sequences associated with each known three-dimensional protein structure.

In a first preferred embodiment of the present invention, the residue variability characteristic that is utilized is solubility variability. Specifically, the hydrophobic and hydrophilic variability of each residue position within different homologous sequences. Each standard amino acid is classified into four classes based on its hydrophobic and hydrophilic variability. The four classes are as follows:

(1) hydrophobic invariant, hydrophilic variant (IV)

(2) hydrophobic invariant, hydrophilic invariant (II)

(3) hydrophobic variant, hydrophilic variant (W)

(4) hydrophobic variant, hydrophilic invariant (VI)

Thus, each of the standard 20 amino acids are classified into 80 amino acid residue variability types where each residue variability type classifies an amino acid residue in accordance with one of the above four classes.

In a second preferred embodiment of the present invention, the focus is on the hydrophilic variability of each residue position within different homologous sequences. Each standard amino acid is classified into each of the following three classes: (1) hydrophilic variant; (2) hydrophilic invariant; and (3) hydrophilic partially variant.

Each of the primary residue sequences 206 that is listed in the intermediate sequence-structure database table 122 is mapped into a corresponding residue variability type sequence 214. The mapping procedure 136 determines a hydrophobic and hydrophilic variability factor for each residue position as a combination of the pair-wise comparisons between each pair of homologous and target sequences. The combined hydrophobic and hydrophilic variability factor for each residue position is then used to classify the corresponding residue into one of the aforementioned four classes.

The hydrophobic and hydrophilic variability factors are calculated in accordance with the following mathematical relations:

$$\text{Hydrophobic Variability}(i) = \sum_{l=2}^{N} \sum_{k=1}^{l-1} \frac{\delta_{H\phi}(n_{ik}, n_{il}) * w_k * w_l}{d_{kl}}$$

$$\text{Hydrophilic Variability}(i) = \sum_{l=2}^{N} \sum_{k=1}^{l-1} \frac{\delta_{HP}(n_{ik}, n_{il}) * w_k * w_l}{d_{kl}}$$

$$\delta_{HP}(n_{ik}, n_{il}) = \begin{cases} 1 \text{ if } n_{ik} \neq n_{il} \text{ and} \\ 0 \text{ otherwise} \end{cases} \begin{pmatrix} n_{il} \in HP \text{ or } n_{ik} \in HP \\ \text{or} \\ n_{ik} \in HA, n_{il} \in HA \end{pmatrix}$$

$$\delta_{H\phi}(n_{ik}, n_{il}) = \begin{cases} 1 \text{ if } n_{ik} \neq n_{il} \text{ and} \\ 0 \text{ otherwise} \end{cases} \begin{pmatrix} n_{ik} \in H\phi, n_{il} \in H\phi \text{ or } HA \\ \text{or} \\ n_{ik} \in HA, n_{il} \in H\phi \end{pmatrix}$$

where N is the number of sequences, i is a residue position, $n_{ik}$ is the ith amino acid of the kth sequence, $d_{kl}$ is a measure of the evolutionary distance between the kth and lth sequences, $w_k$ and $w_l$ are the weights calculated for the kth and lth sequence, $H\phi$ is the set of hydrophobic amino acids, HP is the set of hydrophilic amino acids, and HA is the set of ambivalent amino acids.

Preferably, the PAM distance is used as the measure of the evolutionary distance between two paired sequences, $d_{kl}$, and is calculated from the sequence similarity of two sequences using a lookup table which is described in Dayhoff, M. O., Hunt, L. T., McLaughlin, P. J. & Jones, D. D., *Gene Duplications in Evolution: The Globins*, National Biomedical Research Foundation, Silver Springs (1972), which is hereby incorporated by reference as background information.

Preferably, the weights for each sequence, $w_k$ and $w_l$, are computed in accordance with the method described in Sibbald, P. R. & Argos, P., "Weighting Aligned Protein or Nucleic Acid Sequences to Correct for Unequal Representation," *J. Mol. Biol.* 216, 813–818 (1990) which is hereby incorporated by reference as background information. Briefly, the weighting factor of each sequence is approximately equal to the Voronoi volume of each sequence in sequence space. The sum of the weighting factors for all sequences is unity.

Preferably, the set of hydrophobic amino acids, $H\phi$, includes {Phe, Ile, Leu, Met, Val, Trp}, the set of hydrophilic amino acids, HP, includes {Asp, Glu, Lys, Asn, Gln, Arg, Ser}, and the set of ambivalent amino acids, HA, includes {Ala, Cys, Gly, His, Pro, Thr, Tyr}.

Based on the hydrophobic and hydrophilic variability factors associated with each residue position, each residue is further classified into one of the residue variability types in accordance with the following mathematical relations:

| | |
|---|---|
| Variable Hydrophobic, $V_{H\phi}$: | Hydrophobic variability factor $\geq$ A |
| Invariant Hydrophobic, $I_{H\phi}$: | Hydrophobic variability factor < A |
| Variable Hydrophilic, $V_{HP}$: | Hydrophilic variability factor $\geq$ B |
| Invariant Hydrophilic, $I_{HP}$: | Hydrophilic variability factor < B | wherein A and B are the median hydrophobic and hydrophilic variability factors computed from the entire set of protein sequences associated with the unique protein structures.

The result is a sequence of residue variability types which is then stored in an appropriate entry 214 in the intermediate sequence-structure database 122.

Next, each protein structure 204 in the intermediate sequence-structure database is represented as a one-dimensional environment string 220 (step 406). The environment string is generated from an analysis of the surface area exposure of the residues in the protein structure. This analysis utilizes the three-dimensional coordinates of a protein structure which is obtained from the Protein Data Bank (PDB) 108.

The Hobohm database includes a PDB identifier that indicates an associated entry for the protein structure in the Protein Data Bank 108. The PDB 108 is described in more detail in Bernstein, F. et al, "The Protein Data Bank: A Computer-Based Archival File for Macromolecular Structures," *J. Mol. Biol.* 112, 535–542 (1977), which is hereby incorporated by reference as background information.

The PDB 108 contains the three-dimensional coordinates of protein structures that have been determined by X-ray crystallography or NMR. The three-dimensional coordinates for each selected protein structure (i.e., each protein structure in the intermediate sequence-structure database 122) is then used to determine the degree of exposure of each residue in the protein structure. The ACCESS program 132 can be used to determine the accessible surface areas for each residue from which its relative degree of exposure within the three-dimensional protein structure is determined. ACCESS is described in Lee, B. & Richards, F. M., "The Interpretation of Proteins Structures: Estimation of Static Accessibility," *J. Mol. Biol.* 55, 379–400 (1971), which is hereby incorporated by reference as background information. There are various implementations to the ACCESS program and any of these procedures can be utilized by the present invention. However, the present invention is not limited to ACCESS or its variations, other programs that perform similar functionality can be utilized as well.

The surface area exposure for each residue within a protein structure is determined for each unique protein structure listed in the Hobohm database. The percentage of exposure for each of these residues is then determined as the ratio of the surface area exposure over the maximum exposure for the particular residue. These percentages are then assigned to one of three categories. The three categories are determined based on the exposure percentages of the amino acids in all of the unique proteins structures. The exposure percentages of the amino acids in all of the unique proteins structures are calculated and then sorted in increasing order and partitioned into three equally distributed categories. Each category represents one of the three exposure classes. Two cutoff points are used to delineate the three categories. The lowest category represents a range of surface area percentages that are numerically less than the first cutoff point, $ct_1$; the second category represents a range of surface area exposure percentages that are between the first and second cutoff point, $ct_2$; the third category represents a range of surface area exposure percentages greater than or equal to the second cutoff point.

Thus, the three exposure classes as follows: exposed (E), where the percentage of exposure is greater than or equal to a second cutoff point, $ct_2$; partially exposed or buried (P), where the percentage of exposure is less than the second cutoff point, $ct_2$, and greater than or equal to a first cutoff point, $ct_1$; and buried (B), where the percentage of exposure is less than the first cutoff point, $ct_2$.

Each protein structure is then represented as an environment string consisting of an exposure class for each residue in the structure's primary sequence. This environment string is then stored in the appropriate entry 220 in the intermediate structure-sequence database 122.

Once each selected protein structure in the intermediate sequence-structure database 122 has been characterized as an environment string and its primary residue sequence has been characterized into a corresponding sequence of residue variability types, the scoring matrix 120 (shown in FIG. 2B) can be generated (step 408). The scoring matrix 120 is generated from the residue variability type sequence 214 and environment string 220 of each protein structure 204 stored in the intermediate structure-sequence table 122. Preferably each column of the scoring matrix represents one of the residue variability types and each row of the scoring matrix represents one of the three environmental classes.

The score for each element of the scoring matrix 120 is computed in accord with the following mathematical relation:

score for table entry$(i, j) =$ $$\ln\left\{\left(\frac{\#(rvt_i \text{ in } env_j)}{\sum\limits_{i=1}^{\#env} \#(rvt_i \text{ in } env_l)}\right)\left(\frac{\sum\limits_{k=1}^{\#rvt} \#(rvt_k \text{ in } env_j)}{\sum\limits_{k=1}^{\#rvt} \sum\limits_{l=1}^{\#env} \#(rvt_k \text{ in } env_l)}\right)^{-1}\right\}$$

where the phrase "$\#(rvt_i \text{ in } env_j)$" means the number of occurrences of the ith residue variability type in environment j found in the intermediate sequence-structure database 122.

It should be noted that once the intermediate sequence-structure database 122 and scoring matrix 120 have been generated, these two data structures can be used in accordance with the present invention to predict the three-dimensional numerous target protein strings without having to recompute the intermediate sequence-structure database 122 and scoring matrix 120.

Generation of the Sequence of Residue Variability Types

The second phase of the protein determination procedure 130 maps or converts each target sequence 126 into a corresponding sequence of residue variability types 128. The protein determination procedure 130 can receive as input one or more target sequences 126 for which the procedure 130 will determine an analogous protein structure. For each target sequence 126, a corresponding sequence of residue variability types 128 is generated.

Figure 5:
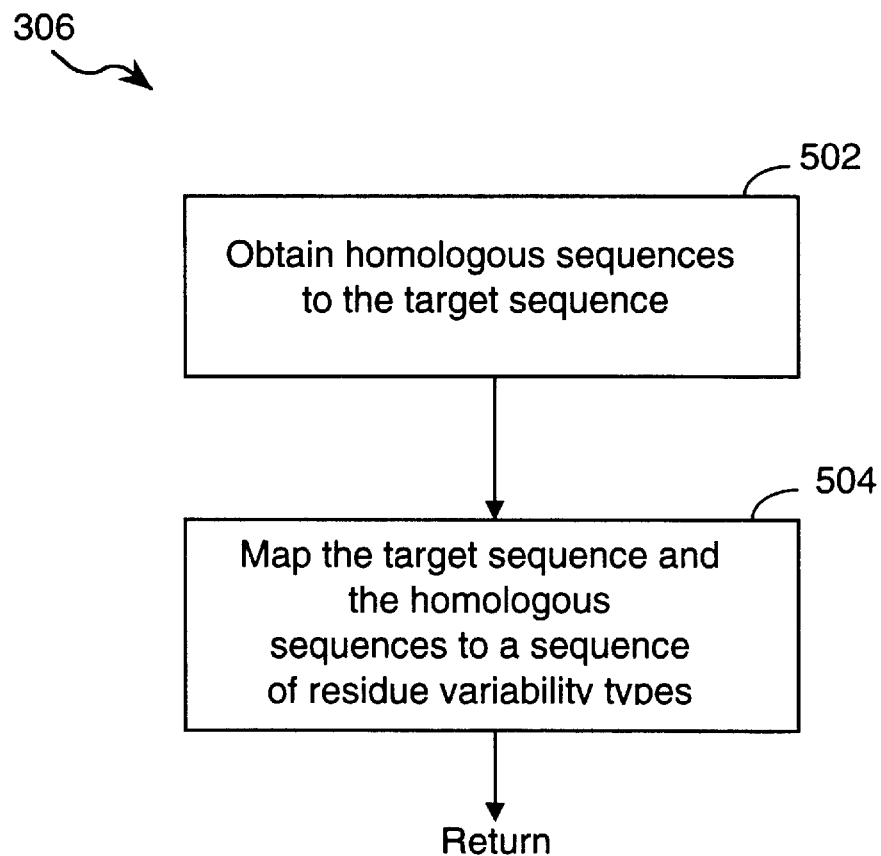
FIG. 5 is a flow chart of the steps used to generate a sequence of residue variability types from a target sequence of amino acid residues in the preferred embodiments of the present invention.

FIG. 5 illustrates the steps used to perform this mapping. For a particular target sequence 126, one or more homologous sequences are selected (step 502). The homologous sequences or multiple sequence alignments are selected from the second sequence alignment database 113 which is the SWISS-PROT database of aligned sequences. This database is described in more detail in Bairoch, A. & Bocckmann, B., "The SWISS-PROT protein sequence data bank," *Nucleic Acid Res.* 19, 2247–2250 (1991), which is hereby incorporated by reference as background information.

Any of the well-known sequence alignment procedures can be used to select the set of homologous sequences for the target sequence. Two such procedures are BLAST or FASTA 138. BLAST is described in Altschul et al., *J. Mol. Biol.* 215, 403–410 (1990) and FASTA is described in Pearson and Lipman, *P.N.A.S.* 85, 2444–8 (1988), both of which are hereby incorporated by reference as background information. Preferably, at least fifteen homologous sequences are selected for each target sequence 126.

The target sequence and its corresponding set of homologous sequences are then used to generate a sequence of residue variability types in the same manner as described above with respect to FIG. 4, step 404 (step 504).

Determination of the Protein Structure

Figure 6:
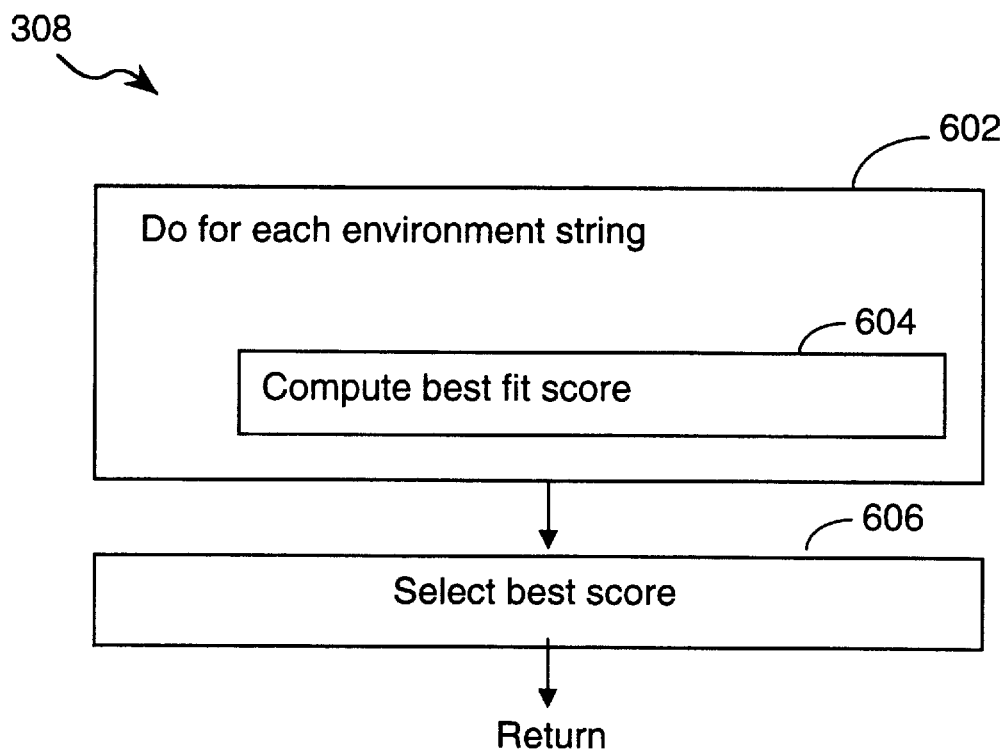
FIG. 6 is a flow chart of the steps used to determine the best match of a target sequence of residue variability types to an environment string of a known protein structure in the preferred embodiments of the present invention.

FIG. 6 illustrates the third phase of the protein structure determination procedure which involves comparing the target sequence with each protein structure (step 602) in order to determine the most likely protein structure that the target sequence folds into.

Next, a best fit score that represents the alignment of the target sequence with an environment string is computed (step 604). Preferably, global alignment is performed using a dynamic programming technique that allows insertions and deletions. Any of the well known dynamic programming procedures can be used. Two such procedures can be found in Needleman, S. B., Wunsch, C. D., *J. Mol. Biol.* 48, 443–453 (1970) and Smith, T. F., Waterman, M. S., *Adv. Appl. Math.* 2, 482–489 (1981), and their application is discussed in M. Gribskov, A. D. McLachlan, D. Eisenberg, *Proc. Natl. Acad. Sci. U.S.A.* 84, 4355 (1987); M. Gribskov, M. Homyak, J. Edenfield, and D. Eisenberg, CABIOS 4, (1988); M. Gribskov and D. Eisenberg, in *"Techniques in Protein Chemistry"* (T. E. Hugli, ed.), p. 108, Academic Press, San Diego, Calif., (1989); M. Gribskov, R. Luthy, and D. Eisenberg, *Meth. In Enz.* 183,146 (1990), all of which are hereby incorporated by reference as background information.

In the preferred embodiments, the dynamic programming procedure 134 defines a score $S_{ij}$ recursively as: where $$S_{ij} = \text{score}(i, j) + \max \begin{bmatrix} S_{i-1,j-1}, \\ \max_{2 \leq k \leq j-1} (S_{i-1,j-k} - w_k), \\ \max_{2 \leq l \leq i-1} (S_{i-l,j-1} - w_l) \end{bmatrix}$$

$S_{ij}$ is the cumulative score, starting at one end of the target sequence, for the alignment of the target sequence with a protein sequence represented by an environment string, such that position i of the target sequence is aligned with position j of the environment string;

score(i,j) is the score obtained from the scoring matrix 120 for the ith residue variability type in the target sequence and the jth environment class value in the environment string;

$W_k$ is the penalty for a gap of length k, as defined below,
$w_l$ is the penalty for a gap of length 1, as defined below.
$p_{open}$ is a gap opening penalty, the value of which may be position dependent,
$p_{extend}$ is a predefined gap extension penalty, the value of which may be position dependent,
$w_k$ and $w_l$ are penalties given by:

$$w_k = p_{open}(j - k) * m_{open} + \sum_{j=j-k}^{j-2} p_{extend}(j) * m_{extend}$$

$$w_l = p_{open}(j - 1) * m_{open} + (l - 1) * p_{extend}(j - 1) * m_{extend}$$

where $m_{open}$ and $m_{extend}$ are global penalty multipliers for the dynamic programming matrix, $p_{open}$ and $p_{extend}$ are position-specific gap opening and gap-extension penalties respectively, k is a gap length representing a number of environment string positions skipped when aligning two adjacent residue variability types in the target string with the environmental string, and l is a gap length representing a number of residue sequence positions skipped when aligning two adjacent environment string positions with residue variability types in the target string. The user can accept default values for $m_{open}$, $m_{extend}$, $p_{open}$ and $p_{extend}$ or set them to predetermined values.

The scores $S_{ij}$ are computed and stored in matrix 124 shown in FIG. 2C starting in the upper left corner of the matrix and proceeding downward and rightward until the value for the matrix entry $S_{max\ i,\ max\ j}$ in the last row and column have been determined. The score $S_{max\ i,\ max\ j}$ represents the best score for aligning the target protein sequence with a particular environment string, and that score 222 is stored in the intermediate structure-sequence database 122 for the corresponding environment string 220 (step 604).

The procedure continues to align each environment string 220 with the target sequence. At the completion of the alignments, the protein structure associated with the highest best fit score 222 is selected as the most likely analogous protein structure (step 606).

The above dynamic programming procedure represents a global alignment strategy. However, the present invention is not limited to this particular type of dynamic programming procedure. A global-local alignment strategy can be used and is described in Fischer, D. & Eisenberg, D., *"Protein fold recognition using sequence-derived predictions,"* Protein Science 5, 947–55 (1996) which is hereby incorporated by reference as background information.

Third Preferred Embodiment

In the third preferred embodiment, residue variability types are defined in different way than the first and second preferred embodiments. The residue variability types in this third preferred embodiment can be called cluster types. Cluster types are defined according to types of amino acid residues found at each position in an aligned set of homologous protein sequences. The clustering classification results from the observation that recurring patterns of residue variation exist in single positions and in short segments of contiguous positions in multiple sequence alignments. These patterns or residue variation provide information that can be used for protein structure prediction.

The clustering version of residue variability classification is based in part on the Han & Baker clusters which are described in Han, K. F. & Baker, D, "Recurring Local Sequence Motifs in Proteins," *J. Mol. Biol.* 251, 176–87 (1995), which is hereby incorporated by reference as background information.

The use of the sequence of cluster residue variability types in step 404 of FIG. 4 with respect to the generation of the scoring matrix and in step 504 of FIG. 5 with respect to mapping the target sequence into a sequence of variability types will be described next. In both of these steps, a residue vector is generated for each position of a multiple sequence alignment. The residue vector represents the frequency of occurrence of each of the 20 common amino acid residues in the respective position. Thus, a residue vector can be represented as a set of 20 values, each representing the relative occurrence frequency of a respective amino acid residue.

A set of N (e.g., 80) cluster-based residue variability types are defined as follows. For every protein structure 204 included in the intermediate structure-sequence database 122 there will typically be a few hundred sequence positions. Since there will typically be at least a few hundred protein structures in the database 122, the database will include tens or hundreds of thousands of residue vectors. Using a well known technique called "vector quantization", the large set of residue vectors can be mapped into a much smaller representative set of cluster vectors. The smaller representative set of vectors are computed so as to minimize the "distance" between the set of input vectors and the representative set of cluster vectors, where "distance" is defined in a manner appropriate to the data being processed. Each distinct cluster vector represents a pattern of residue variability at various positions in sets of homologous protein sequences.

For a description of how vector quantization works, see Robert M. Gray, "Vector Quantization," IEEE ASSP Magazine, pp. 4–29, Apr. 1984, which is hereby incorporated by reference as background information. In the third preferred embodiment, the tens of thousands of residue vectors in the intermediate structure-sequence database 122 are mapped by vector quantization into a set of 80 cluster residue vectors which are herein called cluster residue variability types.

The set of residues found at each aligned sequence position for each protein structure 204 is represented as a residue vector. That residue vector is then compared against each of the 80 cluster residue vectors in order to determine the closest matching cluster vector. The closest matching cluster vector is one that has the smallest distance from the residue vector. The smallest distance can be computed using any of the well known distance calculation techniques such as, but not limited to, the sum of the least squares method. The resulting sequence then consists of a sequence of clusters.

Once the primary sequences in the intermediate structure-sequence database 122 have been mapped into a sequence of cluster residue vectors (i.e., cluster residue variability types), the generation of the scoring matrix 120 proceeds in the same manner as described above. Also, once the target protein sequence has been mapped into a sequence of cluster residue variability types, the computation of the best alignment of the target protein sequence with the protein structures in the intermediate structure-sequence database 122 proceeds in the same manner as described above.

Fourth Preferred Embodiment

In a fourth preferred embodiment of the present invention, an improved level of confidence in the prediction of a protein structure can be achieved by executing the protein structure determination procedure 130 twice with each of the previously described residue variability type classifications. Two predicted protein structures will be generated: a first predicted protein structure is generated as a result of utilizing the solubility residue variability measure; and a second predicted protein structure is generated as a result of utilizing the cluster residue variability measure. The two results are then compared. If both results are the same (i.e., the same protein structure is selected by both procedures), the user is notified that the predicted protein structure lies within a relatively high confidence level.

However, if the two results differ, a structural analysis of the two predicted protein structures is made. The user is then provided with a similarity measure that can be used to determine the extent of the similarities, if any, between the two predicted protein structures.

Figure 7:
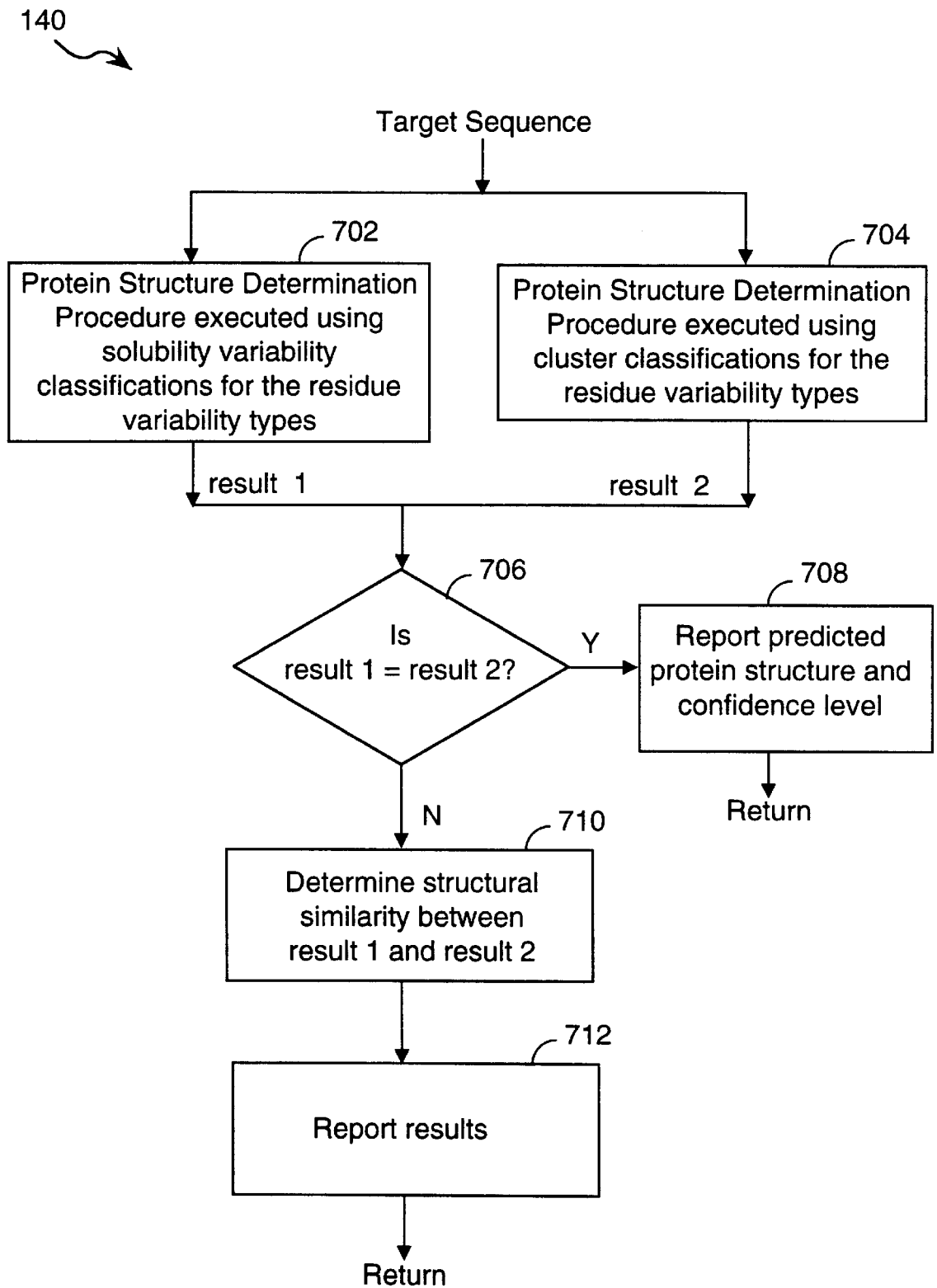
FIG. 7 is a flow chart of the steps used in a fourth preferred embodiment of the present invention.

Referring to FIG. 7, the protein structure determination procedure 130 is executed for a target sequence 126 that utilizes solubility residue variability types and which generates a first result, result 1, indicating a first predicted protein structure (step 702). The protein structure determination procedure 130 is also executed for the same target sequence 126 utilizing cluster residue variability types and which generates a second result, result 2, indicating a second predicted protein structure (step 704). A comparison is made between the two results (step 706). If both results yield the same protein structure (step 706-Y), the user is provided with the predicted protein structure and a high confidence level of the prediction (step 708). In the preferred embodiment the confidence level is approximately 85% when the two results match. More generally, a "high confidence level" may be defined to mean a confidence level of at least 75%.

If the results yield different protein structures (step 706-N), a structural comparison of the two predicted protein structures is performed (step 710). The structural comparison is used to measure the structural similarity between the two predicted protein structures. Various well known techniques exist that can generate such a measurement. Examples include, but are not limited to, root mean square deviation (RMSD) of atomic positions after sequence alignment superposition, similar structural motifs such as secondary structure elements, etc.

Preferably, the structural comparison procedure of Falicov and Cohen is used. This technique is described in detail in Falicov, A, and Cohen, F., "A Surface of Minimum Area Metric for the Structural Comparison of Proteins," *J. Mol. Biol.* 258, 871–892 (1996), which is hereby incorporated by reference as background information. Briefly, the Falicov and Cohen procedure produces a similarity measure based on the smallest possible distance between the virtual backbones of two proteins. This similarity measure (referred to as the Area Functional distance and which is measured in angstroms) can be used to determine the structural similarity between two proteins. An additional measure (referred to as the Fit Comparison ratio) is also provided which is useful for determining the topological similarities between structurally dissimilar proteins.

If the Fit Comparison ratio is less than a prescribed threshold, the two results are considered structurally similar. Preferably, the prescribed threshold is 0.2. Otherwise, if the Fit Comparison ratio is greater than the prescribed threshold, the two results are considered distinct.

The user is provided with the two predicted protein structures, a respective confidence level for each predicted protein structure, a similarity measure, and the fit comparison measure (step 712). When the two results are structurally similar, the two distinct results are reported with an associated confidence level (approximately 85%) that the target protein will have a three dimensional structure that is generally similar to that of the two results.

Although this aforementioned embodiment has been described with respect to executing the protein structure determination procedure twice, it can be easily modified by one skilled in the art to execute any number of times. Each additional execution can utilize an respective set of residue variability types, environment types, or both. For example, a threading procedure based on aligning the known and predicted secondary structure elements of a protein could be used as another threading prediction algorithm to compare against.

Alternate Embodiments

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

The present invention is not limited to the computer system described in reference to FIG. 1. It may be practiced without the specific details and may be implemented in various configurations, or makes or models of distributed computing systems, tightly-coupled processors or in various configurations of loosely-coupled microprocessor systems.

Further, the method and system described hereinabove is amenable for execution on various types of executable mediums other than a memory device such as a random access memory. Other types of executable mediums can be used, such as but not limited to, a computer readable storage medium which can be any memory device, compact disc, or floppy disk.

The present invention is applicable to a number of well-known biochemical and biophysical problems such as but not limited to the inverse protein folding problem and the pair-potentials problem.

Moreover, the environment string can represent any classification scheme that describes the environment of each reside in a known protein structure. Examples of such classification schemes include, but are not limited to, the curvature of a protein's surface and the secondary structure of a protein. For instance, one particular classification scheme that is based on a secondary structure can utilize the following nine environment classes: (1) exposed alpha helix; (2) exposed beta sheet; (3) exposed coil; (4) buried alpha helix; (5) buried beta sheet; (6) exposed coil; (7) partially buried alpha helix; (8) partially buried beta sheet; and (9) partially buried coil.

Although the intended use of the present invention is to match the sequence of an unknown protein structure to the entire fold of a known protein structure, it can be extended to match the unknown sequences to structural domains or sub-domains of known protein structures. This extension involves matching the sequence of an unknown protein to substructures within the fold of known proteins. The matches can be found to more than one of the known protein folds. The probable secondary structure, and perhaps the probable overall fold can be assembled from these disparate matches.

Further, the present invention has been described with reference to certain preferred databases but is not limited to them. Other databases or references that obtain equivalent information can be utilized as well.

Moreover, the present invention has been described with reference to a specific dynamic programming procedure as the preferred threading procedure. However, the present invention is not constrained to this particular type of threading procedure. Others may be used so long as they perform the same functionality as the preferred threading procedure.

Another use of the inventive method that is of significance is verification of protein models. A problem in the determination of protein structure by x-ray crystallography or NMR is being certain that the final protein model is correct. At present, the main method of verification of an x-ray derived protein model is to compare the calculated x-ray pattern to the observed x-ray pattern (the R-factor). Verification of NMR models is a currently developing field. For many protein models determined from energy calculations, homology, or "inspired" guesswork, there is essentially no effective means of verification.

The present invention provides an effective method of verifying a protein model by comparing the environment string from the model with the string of variability types. The scoring matrix is used to evaluate whether the alignment in the model is favorable. A favorable score would be indicative of a homology model which is likely to be correct.

Still another use of the invention is as a screening technique for determining protein sequences that have a structure similar or homologous to the structure of a known sequence. This screening can be done in at least two ways. First, if the 3D structure of a protein is known, the inventive method can be used to align the environment string corresponding to the known 3D structure to other variability residue type strings representing unknown protein structures. This alignment can be used to identity other structural analogs to the known protein structure, as described above. The analogs can then be tested, using known techniques, for a desired biological activity, such as inhibition or stimulation of a receptor. Examples of such inhibition or stimulation are those occurring between a growth factor or a cytokine and their cell-membrane cell-membrane receptors. Those of ordinary skill in the art will know of other protein-receptor relationships to which the inventive screening method can be applied.

Second, if the structure of a protein is not known, the inventive method can be used to determine the most likely protein structure, as described above. Once a compatible 3D structure is determined (which itself is a structural analog to the original protein sequence), that structure can then be used to align the environment string corresponding to the known 3D structure to other variability residue type strings representing unknown protein structures. Closely matching variability residue type strings can be used to identify other structural analogs to the original protein sequence. As described above, the analogs can then be tested for biological function, such as their ability to stimulate or inhibit the interaction between the original protein and a binding partner.

Yet another use of the invention is for building three-dimensional models for protein sequences that have a structure similar or homologous to the structure of a known sequence. A sequence alignment generated from a dynamic programming procedure can be used to overlay the sequence of a known structure, forming essentially a homologous model.

What is claimed is:

1. A computer-implemented method of characterizing a protein sequence's three-dimensional structure, comprising the steps of:

establishing access by a digital data processor to a database of protein sequences having known three-dimensional structures, each protein sequence comprising a sequence of residues, said database including for each protein sequence of known structure a corresponding sequence of residue environment values, each residue environment value representing at least one structural characteristic associated with at least one residue in said sequence of residues;

using the digital data processor:

for a given input protein sequence of unknown three-dimensional structure, identifying a set of homologous protein sequences;

generating for said given input protein sequence and said homologous protein sequences, a corresponding sequence of residue variability types, wherein each residue variability type is selected from a defined set of variability types, each representing a respective positional variability measure of residues associated with various sequence positions in the input and homologous protein sequences;

for each of at least a subset of the protein sequences in said database, selecting an alignment of said generated sequence of residue variability types yielding a highest score in accordance with a predefined scoring method and associating with each said protein sequence in said subset a match score corresponding to said highest score;

selecting a protein structure associated with a protein sequence in said database having a highest match score; and outputting to at least one output device information identifying the selected protein structure.

2. The method of claim 1, said predefined scoring method assigns scores to every defined residue variability type with respect to every defined residue environment value, each score indicating a relative probability that a residue of a respective residue variability type will be found in a portion of any protein structure assigned a respective residue environment value.

3. The method of claim 1,
said structural characteristic indicating a degree of exterior surface area exposure of an associated residue in a corresponding protein sequence.

4. The method of claim 3,
said residue environment values selected from the set consisting of exposed, buried, and partially buried.

5. The method of claim 1,
said positional variability measure includes a solubility variability measure.

6. The method of claim 1,
said generating step further comprising the steps of:
  analyzing solubility variations between residues in similar sequence positions in said given input protein sequence and said selected homologous protein sequences; and
  associating each said solubility variation with a corresponding residue variability type.

7. The method of claim 6,
said solubility variations including hydrophobic variability, hydrophobic invariability, hydrophilic variability, and hydrophilic invariability.

8. The method of claim 6,
said analyzing step further comprising the steps of:
  determining a hydrophobic variability factor and a hydrophilic variability factor for each said residue position, said hydrophobic variability factor determined in accordance with the following mathematical relation:

$$\text{Hydrophobic Variability}(i) = \sum_{l=2}^{N} \sum_{k=1}^{l-1} \frac{\delta_{H\phi}(n_{ik}, n_{il}) * w_k * w_l}{d_{kl}}$$

$$\delta_{H\phi}(n_{ik}, n_{il}) = \left\{ \begin{array}{l} 1 \text{ if } n_{ik} \neq n_{il} \text{ and} \\ 0 \text{ otherwise} \end{array} \left( \begin{array}{l} n_{ik} \in H\phi, n_{il} \in H\phi \text{ or } HA \\ \text{or} \\ n_{ik} \in HA, n_{il} \in H\phi \end{array} \right) \right\}$$

said hydrophilic variability factor determined in accordance with the following mathematical relation:

$$\text{Hydrophilic Variability}(i) = \sum_{l=2}^{N} \sum_{k=1}^{l-1} \frac{\delta_{HP}(n_{ik}, n_{il}) * w_k * w_l}{d_{kl}}$$

$$\delta_{HP}(n_{ik}, n_{il}) = \left\{ \begin{array}{l} 1 \text{ if } n_{ik} \neq n_{il} \text{ and} \\ 0 \text{ otherwise} \end{array} \left( \begin{array}{l} n_{ik} \in HP \text{ or } n_{il} \in HP \\ \text{or} \\ n_{ik} \in HA, n_{il} \in HA \end{array} \right) \right\}$$

where N is the number of sequences,
  i is a residue position,
  $n_{ik}$ is the ith amino acid of the kth sequence,
  $d_{kl}$ is a measure of evolutionary distance between the kth and lth sequences,
  $w_k$ and $w_l$ are weights associated with the kth and lth sequence,
  $H\phi$ is a set of hydrophobic amino acids residues including {Phe, Ile, Leu, Met, Val, Trp},
  HP is a set of hydrophilic amino acids residues including {Asp, Glu, Lys, Asn, Gln, Arg, Ser}, and
  HA is a set of ambivalent amino acids residues including {Ala, Cys, Gly, His, Pro, Thr, and Tyr};
said associating step further comprising the steps of:
  classifying each said residue position in accordance with one of the following classifications:
    hydrophobic variant, if said hydrophobic variability factor>A,
    hydrophobic invariant, if said hydrophobic variability factor<A; and
  classifying each said residue position in accordance with one of the following classifications:
    hydrophilic variant, if said hydrophilic variability factor>B,
    hydrophilic invariant, if said hydrophilic variability factor<B;
wherein A and B are median hydrophobic and hydrophilic variability factors.

9. The method of claim 6,
said solubility variations including hydrophilic variability, hydrophilic invariability, and hydrophilic partially variant.

10. The method of claim 1,
said residue variability types including each amino acid residue classified in accordance with each of four classes selected from the set consisting of (hydrophobic variant, hydrophilic variant), (hydrophobic variant, hydrophilic invariant), (hydrophobic invariant, hydrophilic variant), and (hydrophobic invariant, hydrophilic invariant).

11. The method of claim 1,
said residue variability types including each amino acid residue classified in accordance with each of three classes selected from the set consisting of hydrophilic variant, hydrophilic invariant, and hydrophilic partially variant.

12. The method of claim 1,
said positional variability measure based on a cluster analysis of residue positional variability within a set of multiple sequence alignments corresponding to known protein structures.

13. The method of claim 1,
said generating step further comprising the steps of:
  providing a plurality of cluster vectors, each said cluster vector associated with a particular residue variability type;
  determining a residue vector for each said residue position in said given input protein sequence and said selected homologous protein sequences, each said residue vector indicating a frequency of occurrence of each residue within said residue position;
  matching each said residue vector with a closest cluster vector; and
  representing each said residue position with a residue variability type associated with said matched cluster vector.

14. A computer-implemented method for characterizing a protein sequence's three-dimensional structure, comprising the steps of:
  providing a target sequence of residues of unknown three-dimensional structure;
  using a digital data processor:
    identifying a set of homologous protein sequences for said target sequence;
    mapping said target sequence and said set of homologous protein sequences to a corresponding first sequence of residue variability types, each said residue variability type of said first sequence associated with a first positional variability measure;

mapping said target sequence and said set of homologous protein sequences to a corresponding second sequence of residue variability types, each said residue variability type of said second sequence associated with a second positional variability measure;

determining a first predicted protein structure for said first sequence of residue variability types and a second predicted protein structure for said second sequence of residue variability types;

utilizing said predicted protein structures to determine an analogous protein structure to said target sequence; and outputting to at least one output device information identifying the analogous protein structure.

15. The method of claim 14, providing a plurality of environment strings, each of said environment strings characterizing a protein structure as a sequence of environment classes, each said environment class representing at least one structural characteristic associated with at least one residue in said corresponding protein structure; and said determining step further comprising the steps of:
comparing each of said environment strings with said first sequence of residue variability types in order to determine a first predicted protein structure; and
comparing each of said environment strings with said second sequence of residue variability types in order to determine a second predicted protein structure.

16. The method of claim 15, said structural characteristic corresponding to degree of exterior surface area exposure of an associated residue in a corresponding protein structure.

17. The method of claim 16, said environment classes selected from the set consisting of exposed, buried, and partially buried.

18. The method of claim 14, said utilizing step further comprising the step of:
when said first and second predicted protein structures differ, performing a structural comparison of said predicted protein structures, said structural comparison generating a similarity measure indicating structural similarity of said first and second predicted protein structures.

19. The method of claim 18, reporting each said predicted protein structure and a respective confidence level, wherein said reported confidence level for each reported predicted protein structure is substantially higher when said first and second predicted protein structures match than when said first and second predicted protein structures differ.

20. The method of claim 14, said first positional variability measure including a solubility variability measure of residues associated with various sequence positions in said target sequence and said set of homologous protein sequences.

21. The method of claim 14, said second positional variability measure including a respective measure based on a cluster analysis of residue positional variability within a set of multiple sequence alignments of known protein structures.

22. A computer system for characterizing a protein sequence's three-dimensional structure, said system comprising of:
a memory for storing a database of protein structures, each of said protein structures having a corresponding sequence of residue environment values, each residue environment value representing at least one structural characteristic associated with at least one residue in one of said protein structures, each of said protein structures having a corresponding protein sequence of residues, a set of residue variability types, each of said residue variability types representing a respective positional variability measure of residues associated with various sequences positions in said protein sequences, a given input protein sequence of unknown three-dimensional structure; and a protein structure determination procedure including instructions for identifying a set of homologous protein sequences for said given input protein sequence, converting said given input sequence and said homologous sequences into a corresponding sequence of residue variability types, selecting a best alignment of said sequence of residue variability types with each of at least a subset of said protein structures in said database, including generating a respective match score for said best alignment of said sequence of residue variability types with each of said subset of said protein structures in said database, and select a protein structure associated with a protein sequence in said database having a highest match score.

23. The system of claim 22, said structural characteristic indicating a degree of exterior surface area exposure of an associated residue in a corresponding protein sequence.

24. The system of claim 23, said residue environment values selected from the set consisting of exposed, buried, and partially buried.

25. The system of claim 24, said positional variability measure includes a solubility variability measure.

26. The system of claim 22, said instructions for converting in said protein determination procedure including instructions to analyze solubility variations between residues in similar sequence positions in said given input protein sequence and said selected homologous protein sequences, and associate said solubility variations for each input protein sequence position with a corresponding residue variability type.

27. The system of claim 26, said solubility variations including hydrophobic variability, hydrophobic invariability, hydrophilic variability, and hydrophilic invariability.

28. The system of claim 26, said protein structure determination procedure further including instructions to determine a hydrophobic variability factor and a hydrophilic variability factor for each said sequence position in said given input protein sequence and said selected homologous sequences, said hydrophobic variability factor determined in accordance with the following mathematical relation:

$$\text{Hydrophobic Variability}(i) = \sum_{l=2}^{N} \sum_{k=1}^{l-1} \frac{\delta_{H\phi}(n_{ik}, n_{il}) * w_k * w_l}{d_{kl}}$$

$$\delta_{H\phi}(n_{ik}, n_{il}) = \begin{cases} 1 \text{ if } n_{ik} \neq n_{il} \text{ and} \\ 0 \text{ otherwise} \end{cases} \begin{pmatrix} n_{ik} \in H\phi, n_{il} \in H\phi \text{ or } HA \\ \text{or} \\ n_{ik} \in HA, n_{il} \in H\phi \end{pmatrix}$$

said hydrophilic variability factor determined in accordance with the following mathematical relation:

$$\text{Hydrophilic Variability}(i) = \sum_{l=2}^{N} \sum_{k=1}^{l-1} \frac{\delta_{HP}(n_{ik}, n_{il}) * w_k * w_l}{d_{kl}}$$

$$\delta_{HP}(n_{ik}, n_{il}) = \begin{cases} 1 \text{ if } n_{ik} \neq n_{il} \text{ and} \\ 0 \text{ otherwise} \end{cases} \begin{pmatrix} n_{ik} \in HP \text{ or } n_{il} \in HP \\ \text{or} \\ n_{ik} \in HA, n_{il} \in HA \end{pmatrix}$$

where N is the number of sequences, i is a residue position, $n_{ik}$ is the ith amino acid of the kth sequence, $d_{kl}$ is a measure of the evolutionary distance between the kth and lth sequences, $w_k$ and $w_l$ are weights associated with the kth and lth sequence, Hφ is a set of hydrophobic amino acids residues including {Phe, Ile, Leu, Met, Val, Trp}, HP is a set of hydrophilic amino acids residues including {Asp, Glu, Lys, Asn, Gln, Arg, Ser}, and HA is a set of ambivalent amino acids residues including {Ala, Cys, Gly, His, Pro, Thr, and Tyr};

classify each said residue position of said given input protein sequence in accordance with one of the following classifications:

hydrophobic variant, if said hydrophobic variability factor>A, hydrophobic invariant, if said hydrophobic variability factor<A; and classify each said residue position of said given input protein sequence in accordance with one of the following classifications:

hydrophilic variant, if said hydrophilic variability factor>B, hydrophilic invariant, if said hydrophilic variability factor<B;

wherein A and B are median hydrophobic and hydrophilic variability factors.

29. The system of claim 22, said residue variability types including each amino acid residue classified in accordance with each of four classes selected from the set consisting of (hydrophobic variant, hydrophilic variant), (hydrophobic variant, hydrophilic invariant), (hydrophobic invariant, hydrophilic variant), and (hydrophobic invariant, hydrophilic invariant).

30. The system of claim 22, said residue variability types including each amino acid residue classified in accordance with each of three classes selected from the set consisting of hydrophilic variant, hydrophilic invariant, and hydrophilic partially variant.

31. The system of claim 22, said positional variability measure is based on a cluster analysis of residue positional variability within a set of multiple sequence alignments for known protein structures.

32. The system of claim 22, said converting instructions in said protein structure determination procedure including instructions for providing a plurality of cluster vectors, each said cluster vector associated with a particular residue variability type and representing a pattern of residue variability at various positions in sets of homologous protein sequences, determining a residue vector for each said residue position in said given input protein sequence and said selected homologous protein sequences, said residue vector indicating a frequency of occurrence of distinct residues in said residue position, matching each said residue vector with a closest cluster vector, and representing each said residue position with one of said residue variability types associated with said matched cluster vector.

33. A computer system for characterizing a protein sequence's three-dimensional structure, comprising:

a memory for storing a target sequence of residues of unknown three-dimensional structure, a set of homologous protein sequences for said target sequence, a first set of residue variability types, each said residue variability type of said first set associated with a first positional variability measure, a second set of residue variability types, each said residue variability type of said second set associated with a second positional variability measure;

a protein structure determination procedure including instructions that select one of said sets of residue variability types, map said target sequence and said set of homologous protein sequences to a sequence of said selected residue variability types, and determine a predicted protein structure for said sequence of residue variability types; and a structural comparison procedure for comparing any two specified protein structures, said structural comparison procedure including instructions to generate a similarity measure indicative of structural similarity of said two specified protein structures;

wherein said system executes said protein structure determination procedure a first time utilizing said first set of residue variability types and generating a first predicted protein structure, executes said protein structure determination procedure a second time utilizing said second set of residue variability types and generating a second predicted protein structure, and executes said structural comparison procedure when said first predicted protein structure and said second predicted protein structure differ to generate a measure of structural similarity of said first and second predicted protein structures.

34. The system of claim 33, including a reporting procedure that reports each predicted protein structure and a respective confidence level.

35. The system of claim 33, said structural comparison procedure including instructions to quantify topological differences between said predicted protein structures.

36. The system of claim 33,
    said first positional variability measure including a solubility variability measure of residues associated with various sequence positions in said target sequence and said set of homologous protein sequences.

37. The system of claim 33,
    said second positional variability measure including a respective measure based on a cluster analysis of residue positional variability within a set of multiple sequence alignments of known protein structures.

38. A computer program product for use in conjunction with a computer system, the computer program product comprising a computer readable storage medium and a computer program mechanism embedded therein, the computer program mechanism comprising:
    a database of protein structures, each of said protein structures having a corresponding sequence of residue environment values, each residue environment value representing at least one structural characteristic associated with at least one residue in one of said protein structures, each of said protein structures having a corresponding protein sequence of residues;
    instructions for storing a given input protein sequence of unknown three-dimensional structure; and
    a protein structure determination procedure including instructions for
        identifying a set of homologous protein sequences for said given input protein sequence,
        converting said given input sequence and said homologous sequences into a corresponding sequence of residue variability types, each of said residue variability types selected from a predefined set of residue variability types, each of said residue variability types representing a respective positional variability measure of residues associated with various sequences positions in said protein sequences,
        selecting a best alignment of said sequence of residue variability types with each of at least a subset of said protein structures in said database, including generating a respective match score for said best alignment of said sequence of residue variability types with each of said subset of said protein structures in said database, and
        select a protein structure associated with a protein sequence in said database having a highest match score.

39. The computer program product of claim 38,
    said structural characteristic indicating a degree of exterior surface area exposure of an associated residue in a corresponding protein sequence.

40. The computer program product of claim 38,
    said residue environment values selected from the set consisting of exposed, buried, and partially buried.

41. The computer program product of claim 38,
    said positional variability measure includes a solubility variability measure.

42. The computer program product of claim 38,
    said instructions for converting in said protein determination procedure including instructions to
        analyze solubility variations between residues in similar sequence positions in said given input protein sequence and said selected homologous protein sequences, and
        associate said solubility variations for each input protein sequence position with a corresponding residue variability type.

43. The computer program product of claim 38,
    said solubility variations including hydrophobic variability, hydrophobic invariability, hydrophilic variability, and hydrophilic invariability.

44. The computer program product of claim 38,
    said protein structure determination procedure further including instructions to
        determine a hydrophobic variability factor and a hydrophilic variability factor for each said sequence position in said given input protein sequence and said selected homologous sequences, said hydrophobic variability factor determined in accordance with the following mathematical relation:

$$\text{Hydrophobic Variability}(i) = \sum_{l=2}^{N} \sum_{k=1}^{l-1} \frac{\delta_{H\phi}(n_{ik}, n_{il}) * w_k * w_l}{d_{kl}}$$

$$\delta_{H\phi}(n_{ik}, n_{il}) = \left\{ \begin{array}{l} 1 \text{ if } n_{ik} \ne n_{il} \text{ and} \\ 0 \text{ otherwise} \end{array} \left( \begin{array}{l} n_{ik} \in H\phi, n_{il} \in H\phi \text{ or } HA \\ \text{or} \\ n_{ik} \in HA, n_{il} \in H\phi \end{array} \right) \right\}$$

said hydrophilic variability factor determined in accordance with the following mathematical relation:

$$\text{Hydrophilic Variability}(i) = \sum_{l=2}^{N} \sum_{k=1}^{l-1} \frac{\delta_{HP}(n_{ik}, n_{il}) * w_k * w_l}{d_{kl}}$$

$$\delta_{HP}(n_{ik}, n_{il}) = \left\{ \begin{array}{l} 1 \text{ if } n_{ik} \ne n_{il} \text{ and} \\ 0 \text{ otherwise} \end{array} \left( \begin{array}{l} n_{ik} \in HP \text{ or } n_{il} \in HP \\ \text{or} \\ n_{ik} \in HA, n_{il} \in HA \end{array} \right) \right\}$$

where N is the number of sequences,
i is a residue position,
$n_{ik}$ is the ith amino acid of the kth sequence,
$d_{kl}$ is a measure of the evolutionary distance between the kth and lth sequences,
$w_k$ and $w_l$ are weights associated with the kth and lth sequence,
$H\phi$ is a set of hydrophobic amino acids residues including {Phe, Ile, Leu, Met, Val, Trp},
HP is a set of hydrophilic amino acids residues including {Asp, Glu, Lys, Asn, Gln, Arg, Ser}, and
HA is a set of ambivalent amino acids residues including {Ala, Cys, Gly, His, Pro, Thr, and Tyr};
    classify each said residue position of said given input protein sequence in accordance with one of the following classifications:
        hydrophobic variant, if said hydrophobic variability factor>A,
        hydrophobic invariant, if said hydrophobic variability factor<A; and
    classify each said residue position of said given input protein sequence in accordance with one of the following classifications:
        hydrophilic variant, if said hydrophilic variability factor>B,
        hydrophilic invariant, if said hydrophilic variability factor<B;
wherein A and B are median hydrophobic and hydrophilic variability factors.

45. The computer program product of claim 38,
    said residue variability types including each amino acid residue classified in accordance with each of four classes selected from the set consisting of (hydrophobic variant, hydrophilic variant), (hydrophobic variant, hydrophilic invariant), (hydrophobic invariant, hydrophilic variant), and (hydrophobic invariant, hydrophilic invariant).

46. The computer program product of claim 38, said residue variability types including each amino acid residue classified in accordance with each of three classes selected from the set consisting of hydrophilic variant, hydrophilic invariant, and hydrophilic partially variant.

47. The computer program product of claim 38, said positional variability measure is based on a cluster analysis of residue positional variability within a set of multiple sequence alignments for known protein structures.

48. The computer program product of claim 38, said converting instructions in said protein structure determination procedure including instructions for
providing a plurality of cluster vectors, each said cluster vector associated with a particular residue variability type and representing a pattern of residue variability at various positions in sets of homologous protein sequences,
determining a residue vector for each said residue position in said given input protein sequence and said selected homologous protein sequences, said residue vector indicating a frequency of occurrence of distinct residues in said residue position,
matching each said residue vector with a closest cluster vector, and
representing each said residue position with one of said residue variability types associated with said matched cluster vector.

49. A computer program product for use in conjunction with a computer system, the computer program product comprising a computer readable storage medium and a computer program mechanism embedded therein, the computer program mechanism comprising:
instructions for storing a target sequence of residues of unknown three-dimensional structure;
instructions for identifying a set of homologous protein sequences for said target sequence;
a protein structure determination procedure including instructions that
selects one of at least two sets of residue variability types, said at least two sets of residue variability types including a first set of residue variability types, each said residue variability type of said first set associated with a first positional variability measure, and a second set of residue variability types, each said residue variability type of said second set associated with a second positional variability measure;
maps said target sequence and said set of homologous protein sequences to a sequence of residue variability types from said selected set of residue variability types, and
determines a predicted protein structure for said sequence of residue variability types; and
a structural comparison procedure for comparing any two specified protein structures, said structural comparison procedure including instructions to generate a similarity measure indicative of structural similarity of said two specified protein structures;
wherein said system executes said protein structure determination procedure a first time utilizing said first set of residue variability types and generating a first predicted protein structure, executes said protein structure determination procedure a second time utilizing said second set of residue variability types and generating a second predicted protein structure, and executes said structural comparison procedure when said first predicted protein structure and said second predicted protein structure differ to generate a measure of structural similarity of said first and second predicted protein structures.

50. The computer program product of claim 49, including
a reporting procedure that reports each predicted protein structure and a respective confidence level.

51. The computer program product of claim 49, said structural comparison procedure including instructions to quantify topological differences between said predicted protein structures.

52. The computer program product of claim 49, said first positional variability measure including a solubility variability measure of residues associated with various sequence positions in said target sequence and said set of homologous protein sequences.

53. The computer program product of claim 49, said second positional variability measure including a respective measure based on a cluster analysis of residue positional variability within a set of multiple sequence alignments of known protein structures.

* * * * *